United States Patent [19]

Lewin et al.

[11] Patent Number: 4,486,286

[45] Date of Patent: Dec. 4, 1984

[54] METHOD OF DEPOSITING A CARBON FILM ON A SUBSTRATE AND PRODUCTS OBTAINED THEREBY

[75] Inventors: Gerhard Lewin, West Orange, N.J.; Dan Nir, Haifa, Israel

[73] Assignees: Nerken Research Corp., Brookville, N.Y.; Technion Research & Development Foundation, Ltd., Haifa, Israel

[21] Appl. No.: 425,704

[22] Filed: Sep. 28, 1982

[51] Int. Cl.³ .............................................. C23C 15/00
[52] U.S. Cl. ............................ 204/192 C; 204/192 F; 204/192 E; 204/192 EC; 204/192 R; 428/408
[58] Field of Search ........... 204/192 F, 192 C, 192 E, 204/192 EC; 428/408

[56] References Cited

U.S. PATENT DOCUMENTS 3,840,451 10/1974 Golyanov ..................... 204/192 C
3,961,103 1/1976 Arenberg .......................... 204/298

OTHER PUBLICATIONS

Banks et al., J. Vac. Sci. Tech. 21, 1982, pp. 807–814.
Weissmantel et al., Thin Solid Films C3, (1979), pp. 315–325.
Spencer et al., Appl. Phys. Lett. 29, (1976), pp. 118–120.
Spitsyn et al., J. Crystal Growth 52, (1981), pp. 219–226.
Holland et al., J. Vac. Sci. Tech. 14, (1977), pp. 11–13.
Holland et al., Thin Solid Films 58, (1979), pp. 107–116.
Anderson et al., Thin Solid Films 63, (1979), pp. 155–160.
Morave C., Thin Solid Films 70, (1980), pp. 29–40.

Primary Examiner—Arthur P. Demers
Attorney, Agent, or Firm—Allen R. Kipnes

[57] ABSTRACT

There is disclosed a method for depositing a diamond or diamond-like carbon film on at least one substrate employing a hydrocarbon gas and at least one gas which preferentially removes by chemical sputtering other forms of carbon, especially graphite from said film to thereby obtain useful carbon film coated products.

23 Claims, 1 Drawing Figure

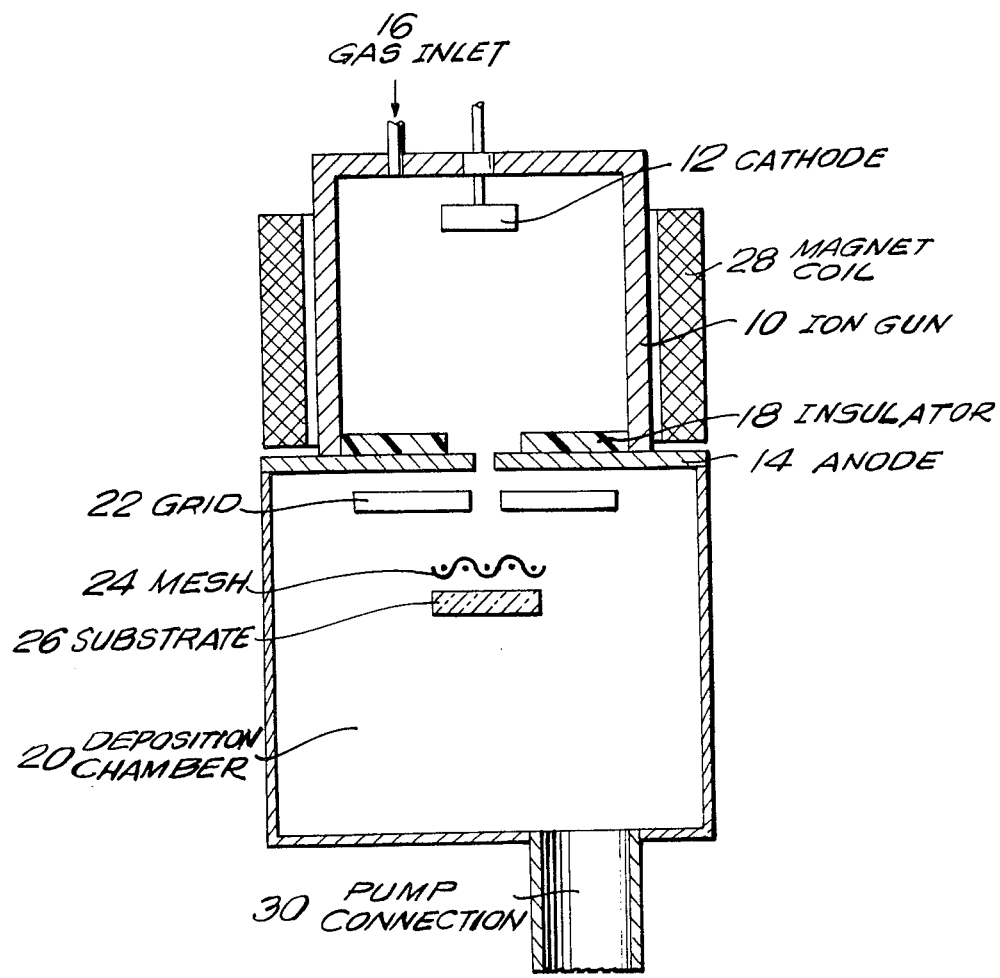

METHOD OF DEPOSITING A CARBON FILM ON A SUBSTRATE AND PRODUCTS OBTAINED THEREBY

BACKGROUND OF THE INVENTION

The present invention relates to a method for depositing a carbon film on a substrate and products obtained thereby.

Moderately energetic ions or neutral atoms of carbon can be used to form a hard film on a substrate. The carbon film is more similar to diamond in properties than to graphite and therefore has been referred to as I (ion) - carbon or diamond-like carbon. The structure of diamond-like carbon is not precisely understood but it is known to be harder than hardened steel though not as hard as diamond. It is also known to be a good insulator, chemically inert, and has a refractive index similar to diamond. However, the specific properties of diamond-like carbon depend on the deposition conditions such as ion energy, substrate temperature and the amount and type of other ions which may impinge on the film.

One application of such films is as hard, protective coatings for optical lenses. Another application is in the medical field for devices which are inserted into the human body. Because the carbon film produced by the process of this invention is chemically inert and an insulator, such coated medical devices possess anti-clotting properties (i.e. do not substantially cause the formation of thrombi). Still further, the present process may be adapted to provide for the homoepitaxial growth of diamonds [See, Nature vol. 275 pp. 634-635 (Oct. 19, 1978)].

Several techniques have been used to develop diamond-like carbon films. For example, J. Appl. Phys. 42, 2953 (1971) discloses the deposition of diamond-like carbon using a carbon-argon beam extracted from an ion source in which an argon glow discharge takes place between an anode and a graphite cathode. This cathode is sputtered by the discharge and some sputtered carbon atoms are ionized in the discharge. A disadvantage of this technique is that the concentration of carbon ions in the discharge is very low. Hence another preferred technique is to crack a hydrocarbon gas in either a DC or radiofrequency (RF) glow discharge. The arrangement in the latter case is analogous to one used in RF sputtering devices. The substrate is placed on an electrode connected to the center conductor of a coaxial cable through a matching network. The substrate assumes a negative bias, the amount of which depends on the power input.

The foregoing techniques produce films which often contain undesirable amounts of graphite which reduces resistance and light transmission and, in large enough concentrations, have an adverse effect on hardness. It appears that as the thickness of the film increases, the proportion of graphite increases because of the formation of graphite nucleation centers.

Additionally, many prior art diamond-like carbon films contain large amounts of hydrogen (about 30 atomic %). This results in compressive mechanical stress and infrared absorption by the film due to C—H bonds. As a result, the thickness of prior art films has not exceeded about one micron.

The prior art techniques as cited above teach that the amount of chemically active gases other than hydrocarbon gases (e.g. $O_2$) should be severely limited to avoid removal of the coating. In contradistinction, applicants have found that ions of these gases preferentially remove undesirable graphite from the substrate film resulting in an improved diamond-like carbon coating.

Since some of the diamond-like carbon is also removed by the graphite removing gases, the amount of these gases must not be excessive. It was generally assumed that these gases must be avoided and must be present in trace amounts, if at all. Contrary to this teaching, Applicants found that these gases improve the coating and can be present in larger amounts without unduly reducing the rate of deposition.

It is therefore an object of the present invention to provide a method of forming a diamond-like carbon film on a substrate which has reduced amounts of graphite and hydrogen. It is a further object of the present invention to provide a diamond-like carbon film which can have thickness exceeding one micron.

SUMMARY OF THE INVENTION

The present invention is directed to a method of forming a diamond-like carbon film on a substrate by providing a source of carbon ions and directing said carbon ions to form a film on a substrate such as an optical lens. The substrate is also exposed to ions which preferentially remove, by chemical sputtering, other undesirable forms of carbon including graphitic carbon from the substrate film. The resulting film is characterized as having a significantly reduced graphite and hydrogen content enabling the formation of stable films having a thickness of greater than one micron.

The carbon ions may be produced by a glow discharge in a hydrocarbon gas. This is often accomplished by a radiofrequency discharge. An alternative way is to use an ion gun with a hydrocarbon gas.

In the radiofrequency discharge the energy of the incident ions varies with the instantaneous value of radiofrequency voltage, the average value depending on the power input. On the other hand, ions guns produce a beam of roughly uniform energy.

The production of carbon ions is carried out by the dissociation and ionization of at least one hydrocarbon gas and at least one gas which preferentially removes graphite from the substrate film by chemical sputtering. Generally, the latter gases are selected from those containing at least one element selected from carbon, oxygen, chlorine, fluorine and hydrogen with the proviso that gases containing only carbon and hydrogen (i.e. hydrocarbon gases) are excluded. The preferred gases for removal of graphite are selected from carbon dioxide, oxygen, carbon monoxide, carbon tetrafluoride, and carbon tetrachloride. These gases have the further advantage of minimizing the build-up of carbonaceous matter on the inside of an ion gun and the electrodes.

Any hydrocarbon gas may be used in the present method but it is preferred to use a gas with a high carbon to hydrogen ratio to reduce the amount of hydrogen present in the discharge. Preferably, the hydrocarbon gas is comprised of at least 40 atomic percent of carbon atoms. The most preferred gases are acetylene and benzene.

If an oxygen containing gas (e.g. $O_2$, $CO_2$, or CO) is selected as the gas which preferentially removes graphitic carbon, it may be necessary to substitute hydrogen gas or a suitable isotope thereof (e.g. deuterium) for some of the oxygen containing gas. This is due to the fact that large amounts of oxygen cause absorption in the infrared around 9.5 micrometers.

The amount of hydrogen gas substituted for the oxygen containing gas is determined by limiting the absorption of infrared radiation of a one micron layer at a wavelength of about 9.5 micrometers to a value of no more than approximately 6–8%.

As a result, the present process permits precise control of the amount of hydrogen in the discharge. This reduces the amount of hydrogen in the film to thereby obtain a film with improved mechanical properties. If necessary, a non-reactive gas such as argon may be used in the present process to stabilize the discharge.

The present process also provides for a substrate temperature between about 100° C. and 200° C. during deposition in order to optimize graphite removal and to improve the mechanical properties of the film.

BRIEF DESCRIPTION OF THE PREFERRED EMBODIMENT

The objects of the invention and advantages associated therewith are more particularly described with reference to the drawing. The drawing and embodiments shown therein are for the purposes of illustration only and are not meant to limit or in any way redefine the invention as claimed in the claims forming part of the application.

The sole FIGURE is a cross-sectional diagram of one embodiment of the depositing system according to the present invention.

Referring to the sole FIGURE, an ion gun apparatus 10 is used containing graphite cathode 12 which is water cooled. The hydrocarbon gas (e.g. acetylene gas) and the gas which preferentially removes graphite by chemical sputtering (e.g. carbon dioxide) enter the ion gun apparatus through gas inlet 16. It is preferable to use acetylene gas and carbon dioxide gas in a pressure ratio of between about 0.5–5.0:1, preferably about 3–1:1 as measured on a thermocouple gauge assuming that the sensitivity of the gauge for these gases is the same as for air. The pressures are measured in the discharge chamber before the discharge is started. During the discharge the pressure is about 50 percent higher. Especially good results have been obtained using a 1:1 ratio. A greater concentration of the hydrocarbon gas may be used in the initial stages of deposition (i.e. up to 500 Angstroms) to improve adherence and then reducing the concentration of hydrocarbon gas to the 1:1 ratio.

Grounded anode 14 is positioned at the end of the ion gun chamber opposite cathode 12. Anode 14 is comprised of a stainless steel plate having a centrally disposed opening, typically about 2 mm in diameter which permits the plasma beam to go through the opening in the anode into deposition chamber 20. The side of anode 14 facing cathode 12 is partially covered by insulator 18 which increases the plasma density at the anode.

The voltage between anode 14 and cathode 12 is generally between about 500 and 800 volts, preferably about 600 volts operating at a current between about 60 and 100 milliamps.

The plasma beam enters deposition chamber 20. Grid 22 with an axially aligned opening relative to anode 14 is positioned about 3 mm therefrom. This grid has a potential of between 50 and 100 volts higher than anode 14 and the plasma beam proceeds through grid 22 to contact substrate 26.

An axial magnetic field of several hundred gauss produced by magnet coil 28 positioned around the ion gun may be applied to increase the path lengths of the electrons in the plasma beam which enables the method to be carried out at a reduced gas density in the ion gun. This effect can be further enhanced by using a cylindrical anode coaxial with the cylindrical wall.

The carbon film formed on substrate 26 is an insulator. Therefore use is made of negatively biased mesh 24 made of stainless steel wires strung in one direction, positioned directly in front of the substrate. At a negative bias of about −1500 volts relative to ground the film on substrate 26 will assume a negative bias of about −200 volts relative to grid 22. This is due to the emission of secondary electrons from mesh 24 when struck by ions of the plasma beam, and the removal of ions from the beam. The voltage of substrate 26 is about −20 volts relative to grid 22 when mesh 24 is floating. The substrate voltage can be further increased by inserting a weak magnetic field perpendicular to the beam between grid 22 and mesh 24 to thereby remove electrons from the beam. When this field is present and the mesh voltage is −150 volts relative to ground, the substrate voltage is only about one volt below the grid voltage. Applicants believe that the average ion energy is almost equal to the potential difference between grid 22 and substrate 26.

In order to insure the formation of a uniform film, substrate 26 is continuously moved in a saw tooth motion perpendicularly to the wires of mesh 24 and the plasma beam. The electron density in the beam can also be increased in a conventional manner by immersing a negatively biased thermionic emitter in the beam.

Residual gases and gases entering through the opening in anode 14 are pumped out of the deposition chamber 20 via pump connection 30. The pressure in the deposition chamber is about $10^{-4}$ torr nitrogen equivalent ion gauge reading.

After conventional cleaning by ion sputtering, it is preferred to employ initially a discharge with an acetylene to carbon dioxide ratio of 3:1 at a total pressure of between about 0.1 and 0.2 torr air equivalent thermocouple gauge reading before discharge. In this initial stage a potential of −1500 volts relative to ground is applied to mesh 24 resulting in a potential of −200 volts relative to grid 22 on substrate 26. The temperature of substrate 26 is maintained at about 150° C. This condition is maintained for about 3 minutes until the coating is about 0.05 micrometer thick.

Thereafter, the amount of acetylene is reduced until a ratio of about 1:1, measured as described above, is obtained and the potential of mesh 24 is increased to between about −100 and −1000 volts relative to ground to obtain a film having a lo negative bias between about −1 and −60 volts with respect to grid 22. In the second stage of operation substrate 26 is maintained at a temperature between about 100° and 150° C. The film is deposited on the substrate at the rate of about one micrometer per hour.

Higher ion energies increase the hardness of the coating and lower energies reduce the absorption. By using the procedure outlined above much lower ion energies can be used without obtaining polymerized hydrocarbon coatings. A higher inital energy also improves adherence of the coating. Various coatings were tested and the following properties were determined.

| | |
|---|---|
| thickness | up to 2 micrometers |
| oxygen content | about 2–2.5 atomic % |
| hydrogen content | about 5 atomic % |
| carbon content | Balance |
| hardness | 1200 kg/mm$^2$ Knoop hardness |

|  | with 10 gram load |
|---|---|
| Severe Abrasion Test (U.S. Military Spec. No. MIL-C-675C) | No effect |
| Electrical resistivity | About $10^{12}$ ohm cm |
| Index of Refraction | 2.3 at 0.7 micrometer about 2.0 in infrared |
| Yellow to brown in visible spectrum and minimum absorption in IR, no C—H bonds observed | |
| Reaction to HF, H₂SO₄ and HNO₃ | NONE |
| Reaction to organic solvents | NONE |
| Heating in vacuum to 500° C. | No effect |

While the foregoing description refers to the use of a single ion gun apparatus other modes of carrying out the present invention may be employed. For example, two ion guns may be used wherein a first ion gun is used for the hydrocarbon gas and a non-reactive gas such as argon to stabilize the discharge. A second gun is used for those gases selected to preferentially remove graphite and other undesirable forms of carbon by chemical sputtering. The guns are positioned at an angle so that the plasma beams resulting therefrom contact at the substrate surface.

Another alternative is to employ an ion gun for the hydrocarbon gas and a non-reactive gas such as argon to stabilize the discharge. A second gun is used for those gases selected to preferentially remove graphite and other undesirable forms of carbon by chemical sputtering, positioned at an angle to permit contact of the respective beams prior to contacting the substrate.

In both embodiments employing two ion guns, the mesh can be dispensed with if one of the ion guns is negatively biased with respect to the other and the substrate is kept in a fixed position.

What we claim is:

1. A method of forming a diamond-like carbon film on a substrate comprising:
   (a) providing a source of carbon ions;
   (b) directing carbon ions to a substrate under conditions producing a diamond-like carbon film which may contain other forms of carbon;
   (c) providing a source of second ions from a non-hydrocarbon gas in greater than an impurity amount capable of preferentially removing said other forms of carbon by chemical sputtering; and
   (d) directing said second ions to said substrate under conditions effective to promote the preferential chemical sputtering of said other forms of carbon in said film.

2. The method of claim 1 wherein said carbon ions and said second ions are simultaneously directed to said substrate.

3. The method of claim 1 wherein said other form of carbon is graphite.

4. The method of claim 1 wherein said second ions are obtained from at least one non-hydrocarbon gas containing at least one element selected from the group consisting of carbon, oxygen, chlorine, fluorine and hydrogen.

5. The method of claim 4 wherein said gases are selected from the group consisting of carbon dioxide, oxygen, carbon monoxide, carbon tetrachloride, carbon tetrafluoride and hydrogen.

6. The method of claim 1 further comprising utilizing a non-reactive gas to stabilize the discharge of said carbon ions and second ions.

7. The method of claim 6 wherein said non-reactive gas is argon.

8. The method of claim 1 further comprising at least one hydrocarbon gas as the source of carbon ions.

9. The method of claim 8 wherein said hydrocarbon gases contain at least 40 atomic percent of carbon.

10. The method of claim 9 wherein said hydrocarbon gases are selected from the group consisting of acetylene and benzene.

11. The method of claim 4 further comprising obtaining said second ions from an oxygen containing gas and adding a hydrogen containing gas in an amount sufficient to limit the absorption of infrared radiation of a one micron film layer at a wavelength of about 9.5 micrometers to a value of no more than about 6 to 8 percent.

12. The method of claim 11 wherein said hydrogen containing gas is selected from hydrogen gas and deuterium.

13. The method of claim 1 wherein acetylene is the source of carbon ions and carbon dioxide is the source of second ions and the pressure ratio of acetylene to carbon dioxide is between about 0.5–5.0:1 as read on a thermocouple gauge calibrated for air before the discharge is started.

14. The method of claim 13 wherein the ratio of acetylene to carbon dioxide is about 3:1 in the initial stages of deposition and is thereafter reduced to about 1:1.

15. The method of claim 1 further comprising heating the substrate to a temperature between about 100° C. and 200° C.

16. The method of claim 1 further comprising producing said carbon ions and said second ions in the same radiofrequency discharge with said substrate.

17. The method of claim 16 wherein said substrate is in contact with a radiofrequency electrode.

18. The method of claim 1 further comprising producing said carbon ions and said second ions in at least one ion-producing source.

19. The method of claim 18 wherein said carbon ions and said second ions are produced in separate ion-producing sources to form first and second plasma or ion beams and contacting said beams at the surface of said substrate.

20. The method of claim 18 wherein said carbon ions and said second ions are produced in separate ion-producing sources to form first and second plasma or ion beams and contacting said beams in front of said substrate.

21. The method of claim 19 or 20 wherein one beam is negatively biased with respect to the other beam.

22. The method of claim 18 further comprising producing a plasma beam containing said carbon ions and electrons and applying a magnetic field substantially perpendicular to said plasma beam to thereby remove a portion of said plasma electrons.

23. A substrate having a diamond-like carbon film produced by the process of claim 1.

* * * * *

UNITED STATES PATENT AND TRADEMARK OFFICE
CERTIFICATE OF CORRECTION

PATENT NO. : 4,486,286

DATED : December 4, 1984

INVENTOR(S) : Gerhard Lewin and Dan Nir

It is certified that error appears in the above—identified patent and that said Letters Patent is hereby corrected as shown below:

Title Page,
Item 56
    left hand column, last line cancel "Arenberg", and insert --Aisenberg--

Right hand column, line 2 cancel "C3", and insert --63--

Column 4, line 50 cancel "lo"

Column 6, line 3 cancel "utilizin", and insert --utilizing-- line 4 cancel "sai", and insert --said-- line 6 cancel "non-reactiv", and insert --non-reactive--

UNITED STATES PATENT AND TRADEMARK OFFICE
CERTIFICATE OF CORRECTION

PATENT NO. : 4,486,286
DATED : December 4, 1984
INVENTOR(S) : Gerhard Lewin and Dan Nir It is certified that error appears in the above—identified patent and that said Letters Patent is hereby corrected as shown below:

Column 6, line 8, cancel "leas" and insert --least-- lines 10 and 12 cancel "hydrocarbo", and insert --hydrocarbon-- line 18 after "of" second occurrence, insert --a-- line 19 cancel "9.", and insert --9.5-- line 20 after "to" second occurrence, and insert --8-- line 64 after "film" insert --thereon, said diamond-like carbon film having an electrical resistivity value of about $10^{12}$ ohm·cm and being--

Signed and Sealed this

Eighteenth Day of June 1985

[SEAL]

Attest:

DONALD J. QUIGG

Attesting Officer    Acting Commissioner of Patents and Trademarks